United States Patent [19]

Kieturakis

[11] Patent Number: 5,549,627
[45] Date of Patent: Aug. 27, 1996

[54] SURGICAL INSTRUMENT AND METHOD FOR APPLYING PROGRESSIVE INTRACORPOREAL TRACTION

[76] Inventor: Maciej J. Kieturakis, 372 Beverly Dr., San Carlos, Calif. 94070

[21] Appl. No.: 327,154

[22] Filed: Oct. 21, 1994

[51] Int. Cl.⁶ .................................................. A61B 17/28
[52] U.S. Cl. ........................................ 606/206; 606/207
[58] Field of Search ................... 606/86–88, 205–211, 606/170

[56] References Cited

U.S. PATENT DOCUMENTS

| | | | |
|---|---|---|---|
| 86,016 | 1/1869 | Howell | 606/207 |
| 936,379 | 10/1909 | Stevens . | |
| 3,096,962 | 7/1963 | Meijs . | |
| 4,191,191 | 3/1980 | Auburn | 128/347 |
| 4,535,773 | 8/1985 | Yoon | 604/51 |
| 4,601,710 | 7/1986 | Moll | 604/165 |
| 4,654,030 | 3/1987 | Moll et al. | 604/165 |
| 4,760,848 | 8/1988 | Hasson | 606/206 |
| 4,836,205 | 6/1989 | Barrett | 128/340 |
| 4,867,404 | 9/1989 | Harrington et al. | 248/231.4 |
| 4,881,537 | 11/1989 | Henning | 604/84 |
| 5,116,353 | 5/1992 | Green | 606/184 |
| 5,147,316 | 9/1992 | Castillenti | 604/164 |
| 5,147,376 | 9/1992 | Pianetti | 606/170 |
| 5,201,325 | 4/1993 | McEwen et al. | 428/779 |
| 5,203,773 | 4/1993 | Green | 606/104 |
| 5,209,736 | 5/1993 | Stephens et al. | 604/164 |
| 5,224,952 | 7/1993 | Deniega et al. | 606/184 |
| 5,226,890 | 7/1993 | Ianniruberto et al. | 604/164 |
| 5,232,451 | 8/1993 | Freitas et al. | 606/174 |
| 5,250,056 | 10/1993 | Hasson | 606/206 |
| 5,258,003 | 11/1993 | Ciaglia et al. | 606/185 |
| 5,271,380 | 12/1993 | Riek et al. | 128/4 |
| 5,279,567 | 1/1994 | Ciaglia et al. | 604/117 |
| 5,284,130 | 2/1994 | Ratliff | 128/20 |
| 5,312,357 | 5/1994 | Buijs et al. | 604/164 |
| 5,334,185 | 8/1994 | Giesy et al. | 604/164 |
| 5,336,237 | 8/1994 | Chin et al. | 606/167 |
| 5,346,504 | 9/1994 | Ortiz et al. | 606/192 |
| 5,348,541 | 9/1994 | Lyell | 604/164 |
| 5,368,598 | 11/1994 | Hasson | 606/119 |
| 5,370,109 | 12/1994 | Cuny | 128/20 |
| 5,425,737 | 6/1995 | Burbank | 606/207 |

Primary Examiner—Michael A. Brown
Attorney, Agent, or Firm—Skjerven, Morrill MacPherson, Franklin & Friel; Norman R. Klivans

[57] ABSTRACT

A surgical instrument for applying intracorporeal traction on tissue in an endoscopic workspace. An elongate introducer sleeve carries a distal jaw structure incorporating cooperating "rolling tracks" with tissue-gripping serrations for applying continuous traction on tissue. A proximal handle includes a jaw-actuating mechanism to close the jaws and the rolling tracks around tissue and to maintain the jaws in any pivoted position. The handle further includes a drive mechanism to roll the rolling tracks. Thus, counter-rotation of the cooperating tracks causes tissue to be progressively gripped and pulled into the "throat" or bore of the introducer sleeve. The handle includes a plurality of flexible bows as a drive mechanism so that the surgeon may rotate the instrument 360° to align the jaws with tissue and thereafter roll the tracks in any angular position by a simple squeezing force.

31 Claims, 6 Drawing Sheets

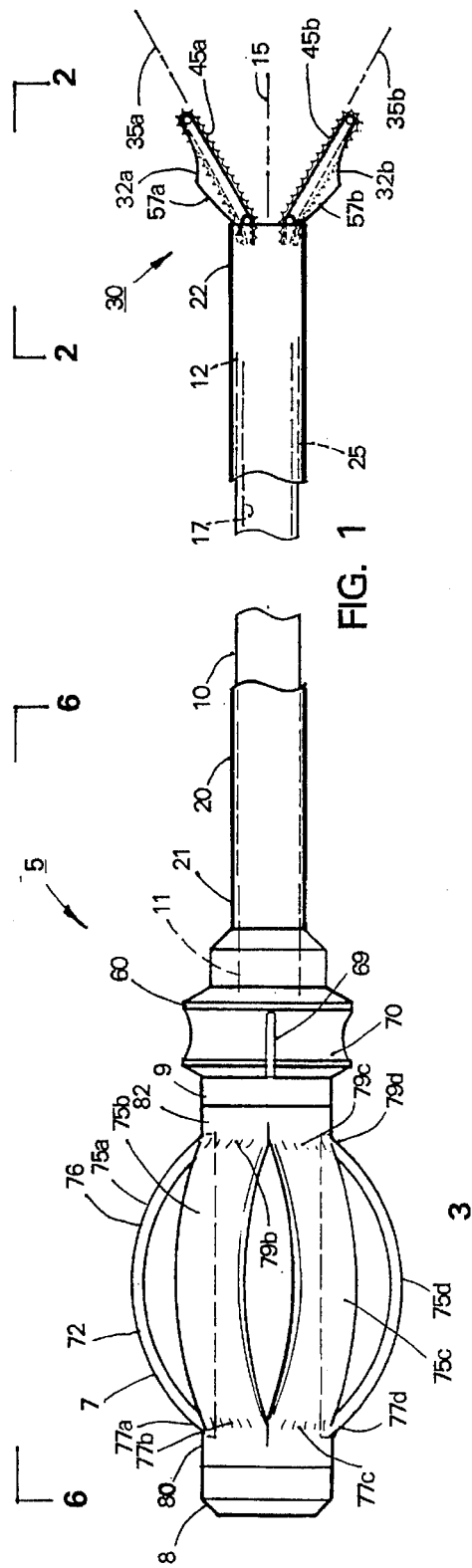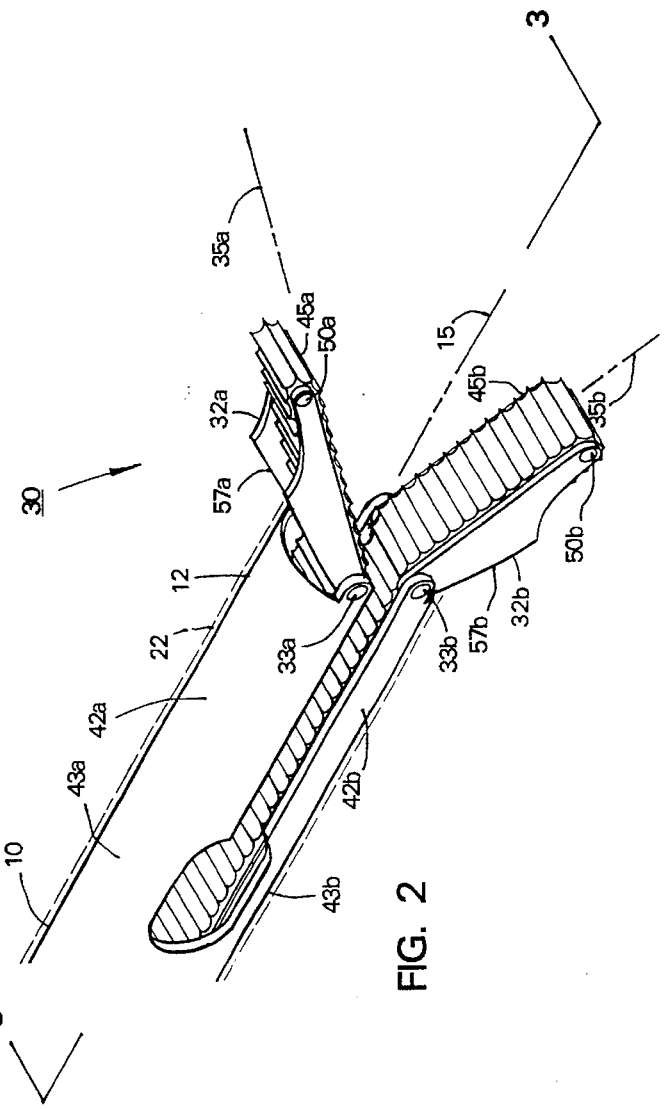
FIG. 1
FIG. 2

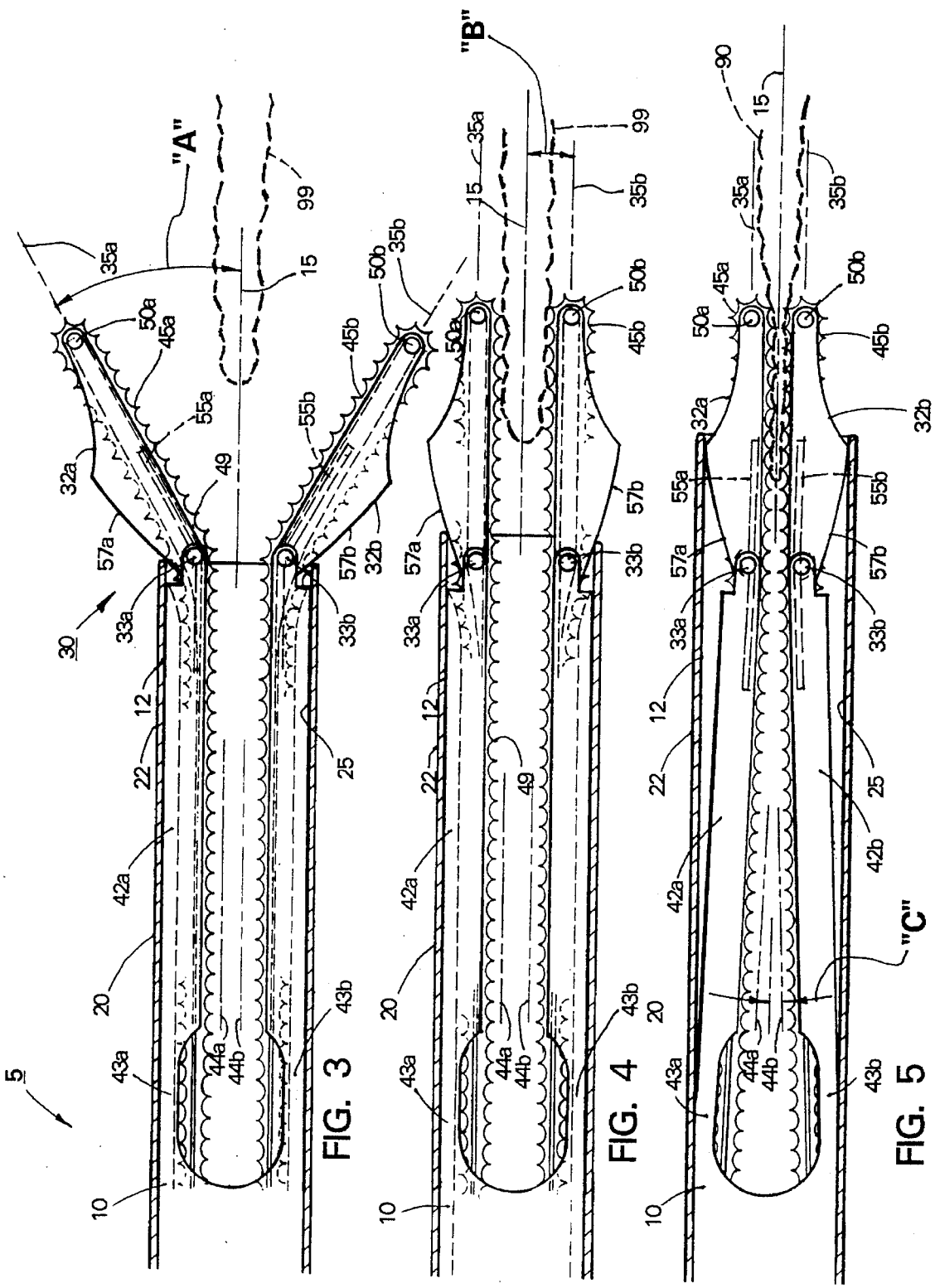

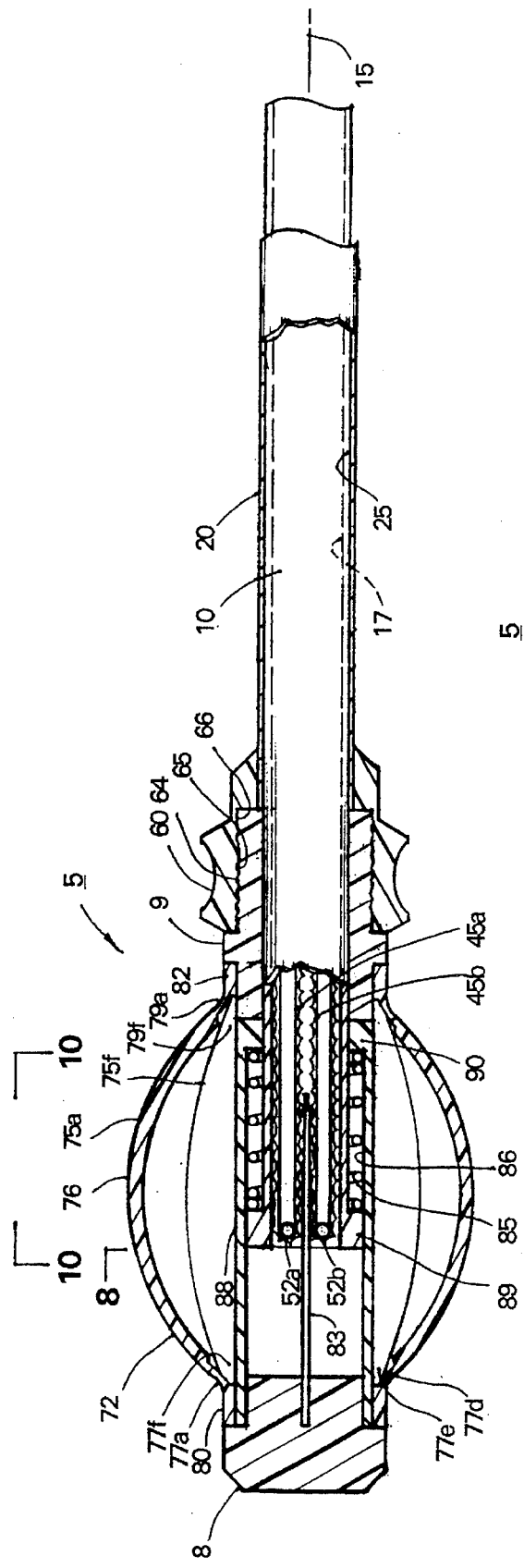
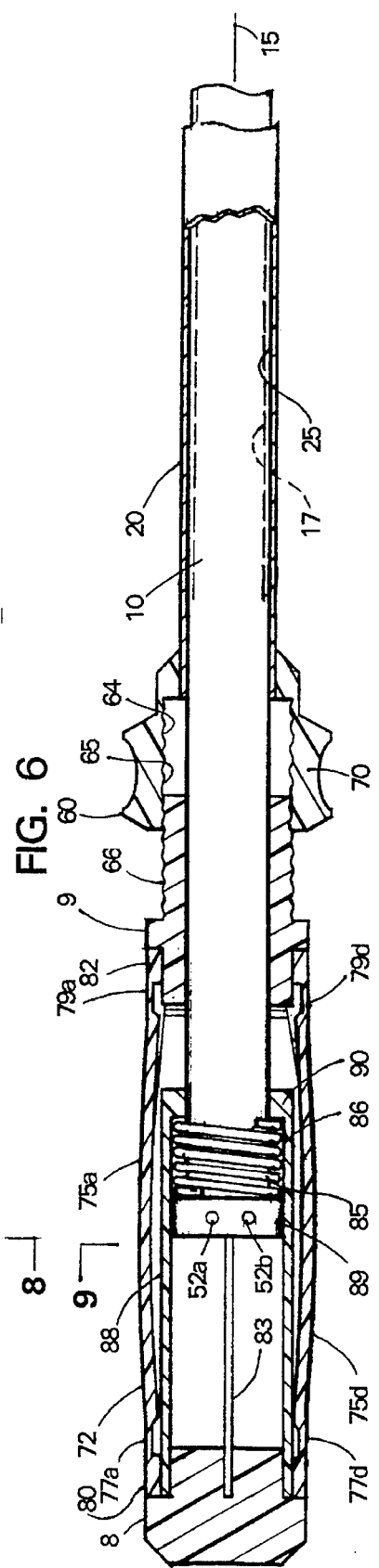
FIG. 6
FIG. 7

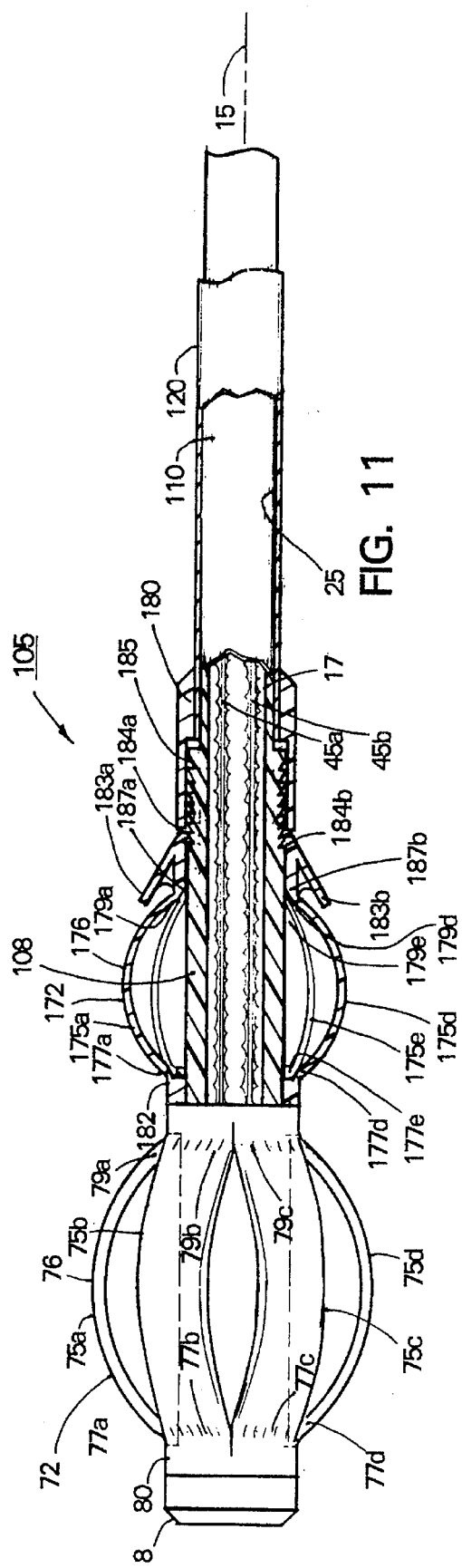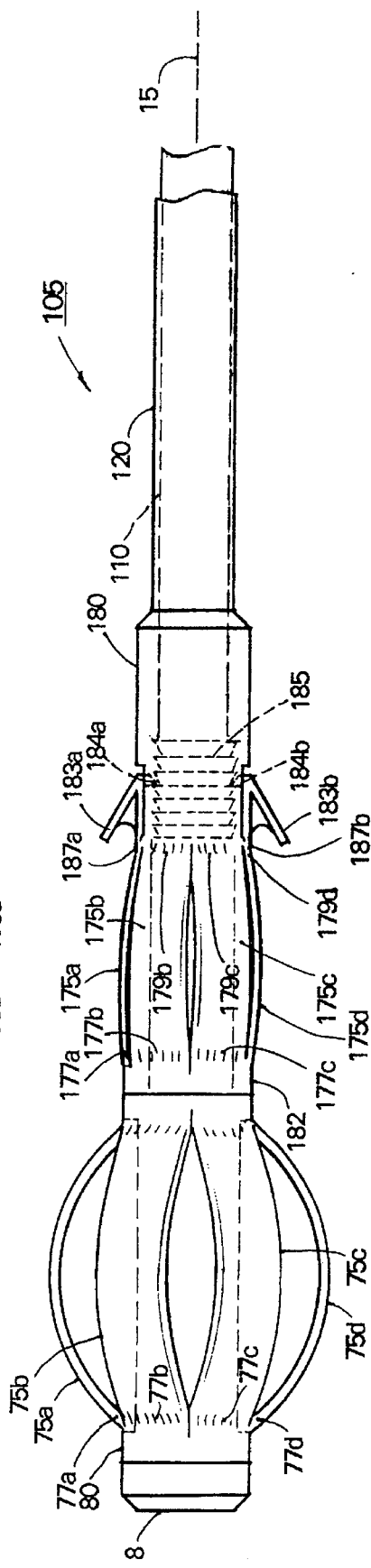

5,549,627

SURGICAL INSTRUMENT AND METHOD FOR APPLYING PROGRESSIVE INTRACORPOREAL TRACTION

BACKGROUND OF THE INVENTION

1. Field of the Invention

This invention relates to surgical instrumentation and more particularly to an instrument and method for gripping and applying intracorporeal traction on tissue in an endoscopic workspace.

2. Description of Prior Art

In a "minimally invasive" endoscopic surgery, for example in the abdominal cavity, instruments for retracting tissue (e.g., grippers) are introduced through cannulas that are in stationary positions in the abdominal wall. Cannulas often are located so that tissue may be retracted axially, that is, by gripping tissue and withdrawing the instrument axially within the cannula. Since there is a limit to how far an instrument may be withdrawn within a cannula, it is often necessary to release and re-grasp tissue. Resilient tissue may rebound when grip is released making it difficult to re-grasp tissue in the desired location. Gripping instruments most often utilize a pistol grip to actuate the instrument's jaws which sometimes requires awkward movements to both rotate the pistol grip align the jaws with tissue and then to actuate the jaws. There is therefore a need for new instruments and methods for applying traction on tissue in an endoscopic workspace.

SUMMARY OF THE INVENTION

In accordance with the present invention for applying traction on tissue in an endoscopic workspace, an instrument includes an elongate introducer sleeve that carries a distal jaw structure incorporating cooperating "rolling tracks" having tissue-gripping serrations for applying continuous traction on tissue. The handle includes a jaw-actuating mechanism to close the jaws and the rolling tracks around tissue and to maintain the jaws in any pivoted position. The handle further includes a track drive mechanism to roll the rolling tracks. Thus, counter-rotation of the cooperating tracks causes tissue to be progressively gripped and pulled into the "throat" or bore of the introducer sleeve. The jaws are double-pivoting whereby the jaw working ends rotate around distal pivots and the jaw forearms rotate around proximal pivots thus providing rolling tracks that remain generally parallel no matter the thickness of the tissue engaged.

The handle includes a 360° drive mechanism that is particularly suitable for endoscopic instruments and includes flexible bows adapted for squeezing. Applying and releasing inwardly-directed force on the bows causes the proximal part of the handle to separate from the distal part of the handle, thus reciprocating a track drive member that rolls the rolling tracks. The handle includes a plurality of opposing bows so that the surgeon may rotate the instrument 360° to align the jaws with tissue and thereafter actuate the drive mechanism in any angular position with a simple squeezing force.

A second embodiment of the traction instrument includes an elongate introducer sleeve with a single "rolling track" that may be pressed against delicate tissue to continuously apply traction. The rolling track is rolled unidirectionally by successively actuating a drive mechanism, thus retracting tissue progressively without axial movement of the instrument. The axis of the rolling track also may be articulated from the axis of the introducer sleeve to better engage tissue planes that lie at an angle relative to that of the introducer sleeve.

In general, the present invention provides an instrument and method for applying progressive intracorporeal traction on tissue without manipulation of the instrument relative to its axis. The present invention provides an instrument and method for applying intracorporeal traction on tissue with a rolling track that incorporates tissue-gripping serrations. The present invention also provides an instrument with cooperating first and second rolling tracks incorporated into a opposing jaws for engaging tissue from opposing sides to apply intracorporeal traction. The present invention provides an instrument with cooperating first and second rolling tracks that retracts tissue into a "throat" or bore of the instrument for removal from an endoscopic workspace.

The present invention provides an instrument for applying intracorporeal traction on tissue that includes a double-pivot jaw structure that maintains the jaw working ends generally parallel from one another to grip tissue uniformly over the jaw working ends regardless of the thickness of the engaged tissue. The present invention also provides an instrument in which the jaw working ends may be releasably locked in any parallel position for any particular thickness of tissue. The present invention provides a handle with a drive mechanism that may be actuated with a single hand by squeezing inwardly on the handle no matter how the handle is rotated.

Additional advantages and features of the invention appear in the following description in which several embodiments are set forth.

BRIEF DESCRIPTION OF THE DRAWINGS

FIG. 1 is an elevational view of a first embodiment of the present invention.

FIG. 2 is an isometric view of a portion of the instrument of FIG. 1 taken along line 2—2 of FIG. 1 rotated 90°.

FIG. 3 is a longitudinal partial sectional view of a portion of FIG. 2 taken along line 3—3 of FIG. 2.

FIG. 4 is a longitudinal partial sectional view similar to FIG. 3 in another position.

FIG. 5 is a longitudinal partial sectional view similar to FIG. 3 in another position.

FIG. 6 is a longitudinal partial sectional view of the handle of the instrument taken along line 6—6 of FIG. 1 rotated 90°.

FIG. 7 is a partial sectional of the handle of FIG. 6 in another position.

FIG. 11 is a partial longitudinal sectional view of an alternative embodiment of a handle and drive mechanism.

FIG. 12 is a partial sectional view of the handle and drive mechanism of FIG. 11 in another position.

DETAILED DESCRIPTION OF THE INVENTION

Figure 8:
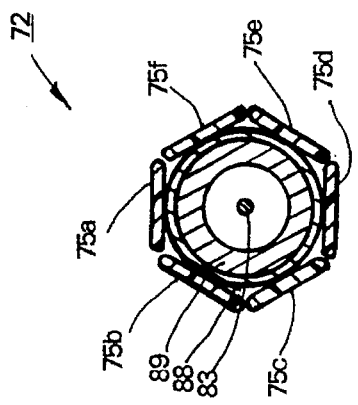
FIG. 8 is a transverse sectional view the handle taken along line 8—8 of FIG. 6.
Figure 9:
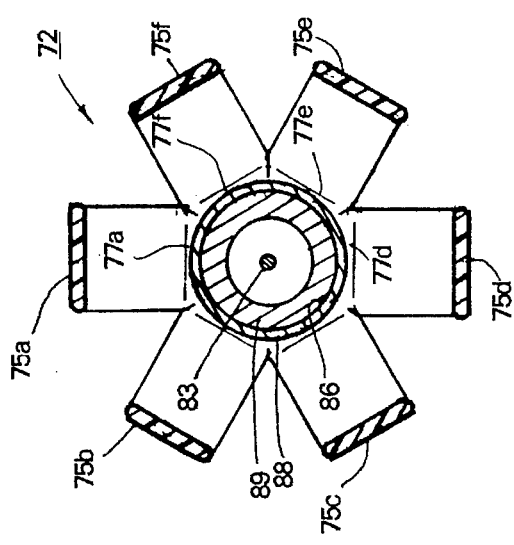
FIG. 9 is a transverse sectional view the handle taken along line 9—9 of FIG. 7.

By way of example, FIG. 1 depicts instrument 5 with plastic handle assembly 7 including proximal handle member 8 and distal handle member 9. Distal handle member 9 is fixed to elongate inner sleeve 10 by adhesives or other suitable means. Inner sleeve 10 with proximal and distal ends 11 and 12, has a cylindrical shape extending along axis 15 with "throat" or bore 17. Sleeve 10 is made of a somewhat flexible plastic such as Delrin®.

Outer sleeve 20 with proximal and distal ends respectively 21 and 22, has a cylindrical shape and defines bore 25 and is slidably disposed around inner sleeve 10. Outer sleeve 20 is made of any suitable material such as thin-wall metal or plastic and has an outer diameter of approximately 10 mm. (not limiting) to cooperate with a standard 10–11 mm. inside diameter cannula.

Still referring to FIG. 1, jaw assembly 30 is incorporated into the distal end 12 of sleeve 10 and includes first and second opposing jaw structures in which each jaw structure is double-pivoting. By double-pivoting it is meant each jaw structure includes a pivotable distal jaw working arm and a pivotable proximal forearm. Referring to FIG. 2, distal jaw working arms 32a and 32b pivot around pins 33a and 33b, respectively. Jaw working arms 32a and 32b are made of any suitable material such as injection-molded plastic and extend along axes 35a and 35b, respectively. As seen in FIG. 2, proximal forearms 42a and 42b are molded portions of the injection-molded inner sleeve 10 and pivot around resilient hinge portions 43a and 43b, although pin-type hinges are within the scope of the invention. Forearms 42a and 42b extend along axes 44a and 44b respectively (see FIGS. 3–5).

The double pivoting of each jaw structure is provided to align jaw working arms 32a and 32b generally parallel with one another as tissue is engaged to evenly distribute pressure over tissue, no matter the thickness of tissue as shown in FIGS. 4–5. The even distribution of engaging pressure is to be contrasted with single pivot jaw structures in which the proximal portion of a jaw closes on tissue before the distal portion of the jaw.

Rolling tracks 45a and 45b are formed in a loop and are made of flexible material such as polyurethane and may be similar to the composite construction of 3 mm. to 6 mm. wide Flex-E-Grip® belts available from W.M. Berg, Inc. of East Rockaway, N.Y. Rolling tracks 45a and 45b are impressed with tissue-gripping serrations 49 molded into the tracks' surfaces. Tracks 45a and 45b are dimensioned in width to fit within bore 17 of inner sleeve 10 and to roll around distalmost rollers 50a and 50b of jaw working arms 32a and 32b. The loops of track 45a and 45b also roll around proximal rollers 52a and 52b within handle 7 (see FIG. 6). A drive mechanism for rolling the tracks 45a and 45b is described in detail below.

A jaw-actuating mechanism is provided to rotate jaw working arms 32a and 32b around their respective pivots, 33a and 33b. The jaw-actuating mechanism also rotates jaw forearms 42a and 42b around their respective pivots 43a and 43b. Referring to FIGS. 2–5, jaw-actuation is provided by the reciprocation of outer sleeve 20 over inner sleeve 10. Referring to FIG. 3, the jaw working arms 32a and 32b, are urged to an open "A" position by torsion springs 55a and 55b. The "A" position of FIG. 3 refers to the maximum angle "A" between instrument axis 15 and jaw working axes 35a and 35b which is approximately 40° (not limiting).

Referring to FIG. 4, the distal sliding of outer sleeve 20 over inner sleeve 10 causes sleeve distal end 22 to contact cam surfaces 57a and 57b of jaw working ends 32a and 32b and to rotate the jaw working ends around their respective pivots, 33a and 33b, to achieve an intermediate closed "B" position. The "B" position of FIG. 4 refers to angle "B" between instrument axis 15 and jaw working axes 35a and 35b which then is 0° or parallel. FIG. 5 illustrates that further distal sliding of outer sleeve 20 causes its distal end 22 to force cam surfaces 57a and 57b inward toward axis 15 as jaw forearms 42a and 42b rotate around their respective hinge portions 43a and 43b, to a fully closed "C" position. The "C" position of FIG. 5 refers to the maximum angle "C" between axis 15 and jaw forearm axes 44a and 44b which is approximately 5° to 10° (not limiting).

The jaw-actuating mechanism, and more particularly the reciprocation of the outer sleeve 20, is operable from handle 7 as shown in FIGS. 1 and 6. Plastic thumb grip 60 is fixed by any suitable means such as adhesives to proximal end 21 of outer sleeve 20. Thumb grip 60 and sleeve 20 are releasably maintainable in any axial position by annular ribs 64 within counterbore 65 in thumb grip 60 that engage cooperating annular indents 66 in the distal reduced-diameter portion 67 of handle member 9 (see FIG. 7). To slide thumb grip 60 over reduced-diameter portion 67, the thumb grip is made of resilient plastic such as Delrin® and a plurality of flexing slots 69 (see FIG. 1) allows proximally-extending portions 70 of the thumb grip to flex radially outward slightly as it is slid to and from over indents 66 (see FIG. 7) of handle member 9.

A drive mechanism is provided to roll the tracks 45a and 45b around distal rollers 50a and 50b, and proximal rollers 52a and 52b. Referring to FIGS. 6–7, the drive mechanism includes bow member 72 with six (not limiting) flexible bows 75a–75f. The flexible bows 75a–75f are portions of a unitary injection-molded resilient plastic bow member 72 in which the intermediate portions 76 of each bow have a uniform thickness to provide uniform bending. The bows have proximal hinge portions 77a–77f, and distal hinge portions 79a–79f, that are reduced in sectional dimension to induce bending at the hinge portion (see FIG. 6). It should be appreciated that bows with pin-type hinges are within the scope of the present invention. The proximal tube portion 80 of bow member 72 is fixed to proximal handle 8. The distal tube portion 82 of bow member 72 is fixed to proximal handle 9. In the sequence of FIGS. 6–7, it can be seen that squeezing any opposing bows 75a–75f, inward toward axis 15 will cause proximal handle member 8 to separate from distal handle member 9. The travel of proximal handle 8 causes drive member 83 to transmit force to tracks 45a and 45b as further described below. A drive mechanism utilizing a plurality of flexible bows allows the surgeon to rotate the handle 360° within one hand to align the jaws with tissue and thereafter to actuate the instrument by a squeezing motion no matter how the instrument is rotated. A squeeze-actuated drive mechanism is to be contrasted with a pistol grip which may require awkward wrist movements to both rotate and actuate the instrument.

The flexible bows 75a–75f are urged to the expanded position of FIG. 6 by compression spring 85 that is disposed around inner sleeve 10 and within bore 86 in telescoping sleeve 88. Referring to FIG. 7, it can be seen that spring 85 exerts pressure on flange 89 of sleeve 10 and flange 90 of telescoping sleeve 88.

Figure 10:
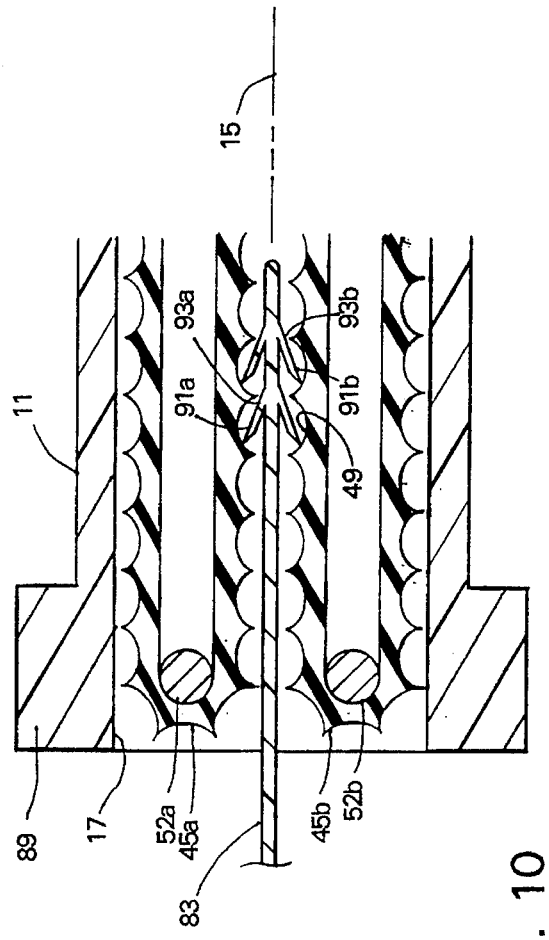
FIG. 10 is an enlarged sectional view of the drive mechanism within the handle taken along line 10—10 of FIG. 6.

Referring to FIGS. 6 and 10, the manner in which the drive mechanism engages tracks 45a and 45b is illustrated. Drive member 83 is made of resilient plastic such as Delrin® that includes resilient spring legs 91a and 91b that are adapted to engage serrations 49 impressed into tracks 45a and 45b (see FIG. 10). As bow member 72 is squeezed causing drive member 83 to travel proximally, spring legs 91a and 91b are in a repose state and engage serrations 49 thereby causing tracks 45a and 45b to roll. As inward pressure on bow member 72 is relaxed, spring 85 moves causes drive member 83 to travel distally and spring legs 91a and 91b bend around hinge portions 93a and 93b respectively to flattened configuration and slide over serrations 49. Drive member 83 may be moved proximally so that spring legs 91a and 91b are proximal from proximal rollers 52a and 52b (see FIG. 10) and out of engagement with the rolling tracks thus permitting the tracks to roll freely to release grip on tissue.

Inner sleeve 10 and outer sleeve 20 of the instrument may be fabricated of transparent medical grade plastic to view the quantity of tissue retracted into bore 17. Jaw arms 32a and 32b and the rolling tracks also may be made of clear plastic. The sides of outer sleeve 20 may have slotted sides (not shown) to cooperate with the space between jaw forearms 42a and 42b (see FIG. 2).

Operation and use of the instrument of FIG. 1 in performing a method in accordance with the present invention can be described briefly as follows with reference to FIGS. 4–5. Preliminarily, the surgeon grasps the instrument in one hand and with his thumb slides thumb grip 60 distally to the "C" position to close jaw working ends 32a and 32b in order to permit the instrument to be introduced through a cannula into an endoscopic workspace. Under conventional endoscopic vision, the surgeon slides thumb grip 60 to the "A" position to open jaw assembly 30. The surgeon then advances jaw working ends 32a and 32b toward tissue to be engaged then slides thumb grip 60 distally to close jaw working ends 32a and 32b on opposing sides of the tissue. The surgeon then may successively apply and release inwardly-directed force on opposing bows 75a–75f thereby causing tissue to be gripped by tracks 45a and 45b and progressively drawn into the "throat" or bore 17 or inner sleeve 10. At any time, the surgeon may re-adjust the closure of the jaw working ends 32a and 32b to suitably grip tissue 99 by sliding thumb grip 60 either proximally or distally.

FIGS. 11–12 illustrate a second embodiment of a gripping instrument 105 in which like reference numbers refer to elements common to the first-described instrument 5. Instrument 105 differs only in the use of a secondary flexing bow drive mechanism for actuating the instrument's jaw structure. This variation of a flexing bow drive includes a locking mechanism. Also the resilient material of the flexing bows has a spring constant to urge the drive mechanism toward the expanded position from the contracted position.

Referring to FIG. 11, distal proximal handle portion 108 of inner sleeve 110 carries secondary bow member 172. The flexible bows 175a–175f are portions of a unitary injection-molded resilient plastic bow member 172 in which the intermediate portions 176 each serve as a leaf-type spring and urge each bow to the expanded position of FIG. 11. The bows have proximal hinge portions 177a–177f, and distal hinge portions 179a–179f, that are reduced in sectional dimension to allow pivoting at the hinge portion (see FIG. 11). The proximal tube portion 180 of bow member 172 is fixed distal handle portion 108 of sleeve 110. The distal tube portion 182 of bow member 172 is fixed to outer sleeve 120. In the sequence of FIGS. 11–12, it can be seen that squeezing any opposing bows 175a–175f, inward toward axis 15 will cause outer sleeve 120 to move distally relative to distal handle portion 108 and sleeve 110 to actuate jaw structure 30.

It should be noted that flexible bows 175a–175f may be made of a spring-type metal with a spring constant incorporated in each such bow. Such metal bows would include a pin-type proximal and distal hinges for pivoting.

Referring to FIGS. 11–12, proximal handle member 8 includes a mechanism for releasably locking bow member 172 in any actuated position between the expanded and contracted positions. Distal tube portion 182 of bow member 172 includes opposing resilient latch arms 180a and 180b, with teeth 184a and 184b that engage one of the annular indents 185 in distal handle portion 108 of sleeve 110. The proximalmost ends of latch arms 180a and 180b may be depressed to pivot around respective resilient pivots 187a and 187b, to lift teeth 184a and 184b out of engagement with annular indents 185 and thus allow the spring constant of flexible bows 175a–175f to return bow member 172 to the expanded position.

Figure 13:
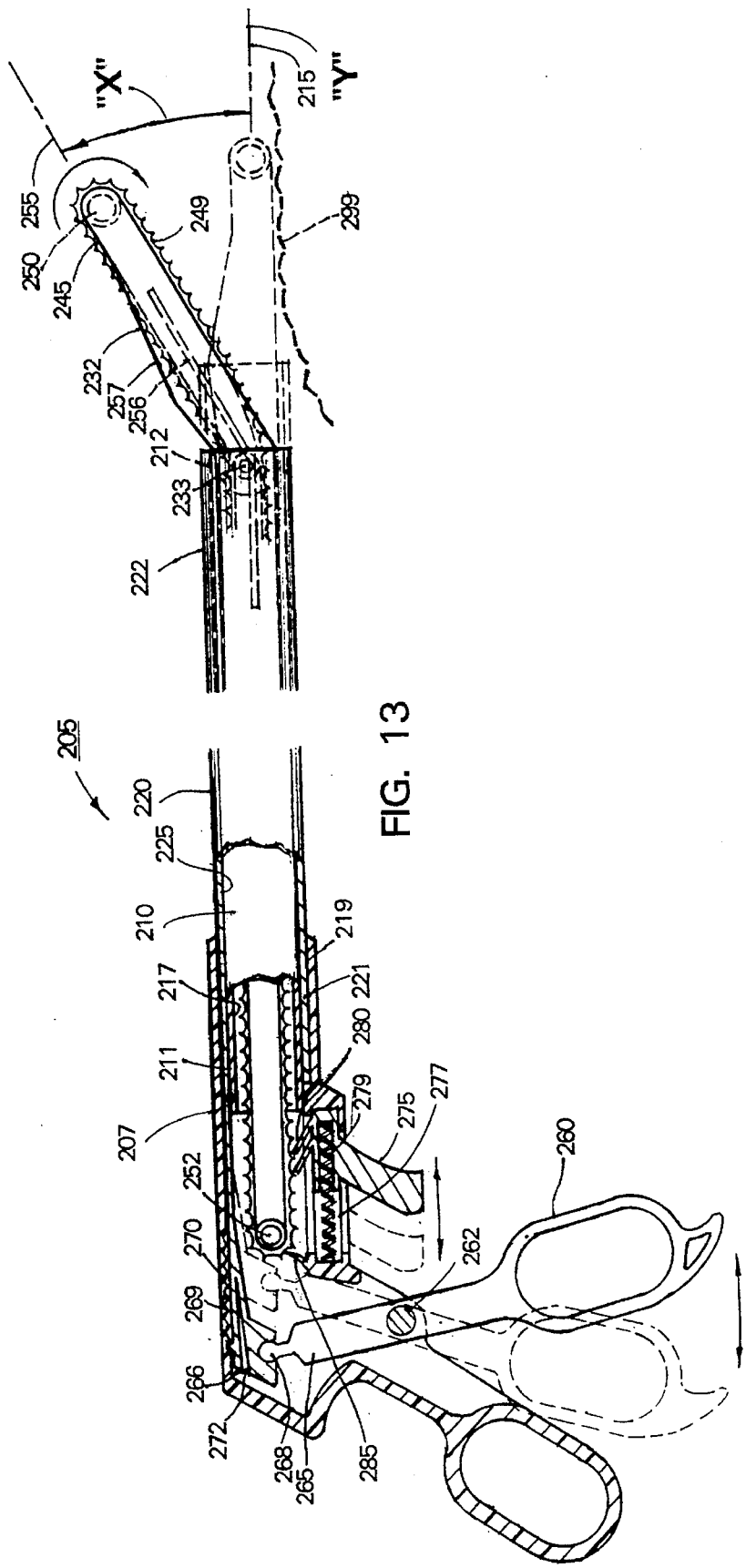
FIG. 13 is a partial sectional view of a second embodiment of the invention.

FIG. 13 depicts a second embodiment of retraction instrument 205 having a single rolling track. Instrument 205 includes plastic handle assembly 207 coupled to inner sleeve 210 that has proximal and distal ends 211 and 212, and extends along axis 215. Sleeve 210 with longitudinal bore 217 is made of any suitable material such as plastic or metal. The proximal end 211 of sleeve 210 is fixed in counterbore 219 of handle 207. Outer sleeve 220 with proximal and distal ends 221 and 222, has a cylindrical shape with bore 225 and is slidably disposed around inner sleeve 210. Outer sleeve 220 has an outside diameter of approximately 10 mm. (not limiting) to cooperate with a standard 10–11 mm. cannula.

Still referring to FIG. 13, track arm 232 is pivotably coupled to distal end 212 of sleeve 210 and rotates around pin 233. Rolling track 245 with serrations 249 is similar the first-described embodiment and rolls around distal roller 250 and proximal roller 252 in handle 207.

An arm-actuating mechanism is provided to articulate track arm 232 around pivot pin 233 to align track arm axis 255 generally parallel to tissue. Referring to FIG. 13, track arm 232 is urged toward the articulated "X" position by torsion spring 256. Track arm 32 may be articulated to the straight "Y" position shown in phantom view by the reciprocation of outer sleeve 220 relative to inner sleeve 210. As sleeve 220 slides in the distal direction over inner sleeve 210, distal end 222 of sleeve 220 abuts cam surface 257 of track arm 232 causing the track arm to pivot around pin 233. Sleeve 220 is slid to and fro over inner sleeve 220 by lever grip 260 rotating around pivot 262 in handle 207. Grip 260 and more particularly its upper lever arm portion 265 is flexibly coupled to proximally-extending tongue 266 that extends from proximal end 211 of plastic outer sleeve 220. The flexible coupling between arm portion 265 and tongue 266 may be any suitable connection and is shown as a ball and socket-type joint 268 that snap-fits together. Sleeve 220 is maintained in any reciprocated position between the "X" and "Y" positions by sharp edge 269 that springably engages cooperating indents 270 that are molded into plastic handle 207. Spring gap 272 in tongue 266 allows resilient plastic edge 269 to flex inwardly toward axis 215 to move between indents 270. Thus, it can be seen that the rotation of lever grip 260 will articulate track arm 32 between the "X" and "Y" positions.

A drive mechanism is provided to roll track 245 around proximal and distal rollers respectively 250 and 252. The drive mechanism includes plastic trigger 275 made of a resilient plastic such as Delrin® that is slidably disposed in slot 277 molded into handle 207. Compression spring 279 urges trigger 275 to its distalmost position. Slanted resilient plastic spring legs 280 are molded into trigger 275 and are adapted to engage serrations 246 in track 245 as the trigger is depressed (proximally) thus causing the track to roll in a clockwise direction as seen in FIG. 13. As trigger 275 is released and is urged distally by compression spring 279, the resilient ratchet legs 280 flex away from axis 215 and slide over serrations 246 in track 245. A mechanism is provided to prevent track 245 from rolling counter-clockwise in the view of FIG. 13 and includes resilient plastic cog 285 molded into handle 207. Cog 285 flexes outwardly as serrations 246 pass underneath it when the track rolls in a clockwise direction as seen in FIG. 13 and thereafter cog 285 will flex inwardly to engage serrations 249 to prevent track 45 from rolling counter-clockwise as trigger 65 is released.

Operation and use of the instrument of FIG. 13 in performing a method in accordance with the present invention can be described briefly as follows. The surgeon moves lever grip 260 to the "Y" position thereby causing the axis 255 of track arm 232 to be aligned with instrument axis 215. The surgeon then may introduce the straightened instrument through a cannula into the endoscopic workspace. Under endoscopic vision, the surgeon may move lever grip 260 to articulate track arm 232 to make it generally parallel to tissue 299 as he presses track 245 gently into tissue. Thereafter, the surgeon sequentially depresses and releases trigger 275 causing track 245 to roll thereby progressively applying intracorporeal traction on tissue without any axial movement of the instrument.

This disclosure is illustrative and not limiting. Other variations will be apparent as for example an instrument having short rolling tracks that roll only around the jaw working ends together with an elongate flexible drive member that extends through the instrument to engage the tracks. Other mechanisms will be apparent for rolling the tracks such as mechanical means for rotating the rollers that engage the tracks. Also, the jaws may be actuated by conventional extension members that are connected to a lever arm on each jaw. Also, the distal end of the instrument's introducer sleeve may have a flexible universal joint as disclosed in the above-referenced application "Endoscopic Surgical Instrument". Further variations will be apparent to one skilled in the art in light of this disclosure and are intended to fall within the scope of the appended claims.

What is claimed is:

1. A surgical instrument for applying traction on tissue, comprising:

an elongate introducer member;

at least one rolling track for engaging tissue incorporated into a distal end of said introducer member; and a track drive mechanism operatively connected to said rolling track.

2. The instrument of claim 1, wherein said rolling track has serrations on its surface.

3. The instrument of claim 2, wherein said track drive mechanism comprises a drive member reciprocating along a longitudinal axis defined by said introducer member and at least one cooperating flexible member engaging said serrations on the surface of said rolling track, thereby rolling said rolling track.

4. The instrument of claim 1, wherein said rolling track is flexible.

5. A surgical instrument for applying traction on tissue, comprising:

an elongate introducer member;

an arm structure having at least a first arm working end associated with a distal end of said introducer member;

a rolling track adapted to engage tissue and incorporated into said first arm working end; and a track drive mechanism operatively connected to said rolling track.

6. The instrument of claim 5, wherein said arm structure includes:

a first pivot associated with said distal end of said introducer member around which said first arm working and rotates; and an arm structure actuating mechanism thereby causing said first arm working end to rotate around said first pivot.

7. The instrument of claim 5, wherein said track drive mechanism includes a reciprocating drive member having a resilient portion that engages cooperating indentations in said rolling track.

8. The instrument of claim 7, wherein said track drive mechanism further comprises:

a plurality of longitudinally-extending flexible bow elements each moveable between a first position wherein said bow elements are flexed outward away from said axis and a second position wherein said bow elements are flexed inward toward said axis, said flexible bow elements being connected to said reciprocating drive member whereby movement between said first and second positions causes proximal and distal travel along a longitudinal axis defined by said introducer member of said reciprocating drive member.

9. The instrument of claim 8, wherein said plurality of bow elements define a structure having symmetry in 360° relative to a longitudinal axis of said introducer member.

10. The instrument of claim 5, further comprising an arm structure locking mechanism operatively connected to said arm structure, thereby locking said first arm working end in any rotated position.

11. The instrument of claim 5, wherein said first pivot is a unitary resilient hinge.

12. The instrument of claim 11, wherein said hinge is of plastic.

13. The instrument of claim 5, wherein said first pivot is a pin-type hinge.

14. The instrument of claim 5, said arm structure further comprising a second arm working end opposing said first arm working end, said second arm working end rotating around a second pivot associated with said distal end of said introducer member; and an arm-actuating mechanism rotating both said first and second arm working ends on their respective first and second pivots thereby to move said first and second arm working ends towards and away one another.

15. The instrument of claim 14, further comprising a rolling track adapted to engage tissue incorporated into said second arm working end.

16. The instrument of claim 15, further comprising a track drive mechanism operatively connected to each said rolling track.

17. The instrument of claim 14, wherein said arm structure includes a first proximal arm portion and a second proximal arm portion connected respectively to said first arm working end and said second arm working end, and a third pivot and a fourth pivot respectively connecting said first and second proximal arm portions to said distal end of said introducer member.

18. A surgical instrument comprising:

an elongate introducer member;

an arm structure coupled to a distal end of said introducer member, said arm structure including:

first and second cooperating jaw elements each having a proximal forearm and a distal working end, each forearm rotating around a primary pivot coupled to said distal end of said introducer member, each working end being pivotably connected to a respective forearm by a secondary pivot;

a working end-actuation mechanism coupled to each working end, thereby causing each working end to separate from and converge toward one another around its secondary pivot; and a forearm-actuation mechanism coupled to each forearm, thereby causing each working end to separate from and converge toward one another around its primary pivot.

19. The instrument of claim 18, further comprising a rolling track coupled to each working end.

20. The instrument of claim 18, further comprising a track drive mechanism operatively connected to each rolling track.

21. The instrument of claim 18, further comprising an arm structure locking mechanism operatively connected to said arm structure, thereby locking said arm structure in any one of a plurality of rotated positions relative to the pivots.

22. The instrument of claim 18, wherein said introducer member is at least partly of transparent material.

23. A surgical instrument that engages tissue, comprising:

an extension member;

a jaw structure with first and second jaws respectively having first and second proximal portions and first and second distal working ends, and each proximal portion rotating around an associated primary pivot associated with a distal end of said extension member, each working end being pivotably connected to the associated proximal portion by a secondary pivot;

a working end-actuation mechanism operatively connected to said first and second working ends thereby to rotate said first and second working ends around said secondary pivots, thereby causing said first and second working ends to separate from and converge toward one another; and a proximal portion-actuation mechanism operatively connected to said first and second jaws thereby to rotate said first and second jaws around said primary pivots and thereby causing said first and second working ends to further separate from and converge toward one another.

24. The instrument of claim 23, wherein each said secondary pivot is a unitary resilient hinge.

25. The instrument of claim 23, wherein each said secondary pivot is a pin-type hinge.

26. A drive system for a surgical instrument for transmitting force to an actuatable working structure of the surgical instrument, comprising:

an extension member defining an axis;

a drive member operatively connectable to said working structure;

a drive mechanism connected to said drive member and associated with said extension member, said drive mechanism comprising a plurality of longitudinally-extending flexible bow elements operatively connected to said drive member and each bow element being moveable between a first position wherein said bow elements are flexed outward away from said axis, and a second position wherein said bow elements are flexed inward toward said axis, whereby movement between said first and second positions causes proximal and distal axial travel of said drive member transmitting force from said drive mechanism to said working structure.

27. The instrument of claim 26, wherein said flexible bow elements are urged toward the first position from the second position by a spring force within said flexible bow elements.

28. The instrument of claim 26 wherein said flexible box elements are urged toward the first position from the second position by a spring associated with said extension member.

29. The instrument of claim 26, further comprising a drive mechanism lock operatively connected to said drive mechanism, thereby locking said drive mechanism in any one of a plurality of positions between said first and second positions.

30. A method of applying traction to tissue in an endoscopic workspace, comprising:

introducing a distal end of an introducer that incorporates a rolling track adapted for engaging tissue into said workspace proximate to said tissue;

pressing said rolling track against said tissue to engage said tissue; and rolling said rolling track, thereby applying traction on said tissue.

31. A method of applying traction on tissue in an endoscopic workspace, comprising:

introducing a distal end of an introducer into said workspace proximate to said tissue, wherein said distal end includes first and second pivotable opposing jaws each having a rolling track;

closing said opposing pivotable jaws around said tissue; and rolling said rolling tracks, thereby applying traction on opposing sides of said tissue.

* * * * *